United States Patent [19]

Swerdloff et al.

[11] Patent Number: 5,528,650

[45] Date of Patent: Jun. 18, 1996

[54] METHOD AND APPARATUS FOR RADIATION THERAPY

[76] Inventors: Stuart Swerdloff, 2309 Upham St., Madison, Wis. 53704; Thomas R. Mackie, 2310 Ravenswood Rd., Madison, Wis. 53711; Timothy Holmes, 12 Coronado Ct. #2, Madison, Wis. 53705

[21] Appl. No.: 191,243

[22] Filed: Feb. 2, 1994

Related U.S. Application Data

[62] Division of Ser. No. 854,521, Mar. 19, 1992.

[51] Int. Cl.$^6$ ............................................. A61N 5/10
[52] U.S. Cl. ..................................... 378/65; 378/69
[58] Field of Search ............................ 378/64, 65, 68, 378/69

[56] References Cited

U.S. PATENT DOCUMENTS

| | | | |
|---|---|---|---|
| 3,783,251 | 1/1974 | Pavkovich | 364/413.26 |
| 4,794,629 | 12/1988 | Pastyr et al. | 378/152 |
| 4,817,125 | 3/1989 | Sklebitz | 378/152 |
| 4,868,843 | 9/1989 | Nunan | 378/152 |
| 4,868,844 | 9/1989 | Nunan | 378/152 |
| 4,905,268 | 2/1990 | Mattson et al. | 378/158 |
| 4,987,309 | 1/1991 | Klasen et al. | 250/492.1 |
| 5,297,037 | 3/1994 | Ifuku | 364/413.15 |
| 5,317,616 | 5/1994 | Swerdloff et al. | 378/65 |
| 5,351,280 | 9/1994 | Swerdloff et al. | 378/65 |
| 5,394,452 | 2/1995 | Swerdloff et al. | 378/65 |

OTHER PUBLICATIONS

Calculation and Application of Point Spread Functions For Treatment Planning With High Energy Photon Beams, Ahnesio et al., Acta Oncol. 26:49–56; 1987.

Methods of Image Reconstruction From Projections Applied to Conformation Radiotherapy, Bortfeld et al., Phys. Med. Biol. 35(10), 1423–1434; 1990.

Feasibility Solutions in Radiation Therapy Treatment Planning, Altschuler et al., IEEE Comp. Soc. 1984: 220–224.

Optimization of Stationary and Moving Beam Radiation Therapy Techniques, Brahme, Radiotheraphy and Oncol. 12:129–140; 1988.

A Unified Approach to the Optimization of Brachytherapy and External Beam Dosimetry, Holmes et al., Int. J. Radiation Oncology Biol. Phys., vol. 20, pp. 859–873, 1991.

*Primary Examiner*—David P. Porta
*Assistant Examiner*—David Vernon Bruce

[57] ABSTRACT

A radiation therapy apparatus includes a compensator having a plurality of leaves to divide the radiation beam into rays each of which may be effectively and individually attenuated over a range of attenuations by controlling the duty cycle of the leaves position between the open and closed states. An apparatus for controlling the compensator accounts for scattering of radiation through the deconvolution of a terma map and calculates a sinogram for controlling the compensator at a variety of angles about a patient using iterated forward and back projections efficiently calculated in frequency space.

10 Claims, 7 Drawing Sheets

METHOD AND APPARATUS FOR RADIATION THERAPY

This is a division of application Ser. No. 07/854,521, filed Mar. 19, 1992.

BACKGROUND OF THE INVENTION

1. Field of the Invention

This invention relates generally to radiation therapy equipment for the treatment of tumors, or the like, and specifically to a compensator mechanism and associated radiation therapy planning software for regulating the dose of radiation within irregularly shaped zones within the patient.

2. Background Art

Medical equipment for radiation therapy treats tumorous tissue with high energy radiation. The dose and the placement of the dose must be accurately controlled to insure both that the tumor receives sufficient radiation to be destroyed, and that damage to the surrounding and adjacent non-tumorous tissue is minimized.

Internal-source radiation therapy places capsules of radioactive material inside the patient in proximity to the tumorous tissue. Dose and placement are accurately controlled by the physical positioning of the isotope. However, internal-source radiation therapy has the disadvantages of any surgically invasive procedure, including discomfort to the patient and risk of infection.

External-source radiation therapy uses a radiation source that is external to the patient, typically either a radioisotope, such as $^{60}Co$, or a high energy x-ray source, such as a linear accelerator. The external source produces a collimated beam directed into the patient to the tumor site. External-source radiation therapy avoids some of the problems of internal-source radiation therapy, but it undesirably and necessarily irradiates a significant volume of non-tumorous or healthy tissue in the path of the radiation beam along with the tumorous tissue.

The adverse effect of irradiating of healthy tissue may be reduced, while maintaining a given dose of radiation in the tumorous tissue, by projecting the external radiation beam into the patient at a variety of "gantry" angles with the beams converging on the tumor site. The particular volume elements of healthy tissue, along the path of the radiation beam, change, reducing the total dose to each such element of healthy tissue during the entire treatment.

The irradiation of healthy tissue also may be reduced by tightly collimating the radiation beam to the general cross section of the tumor taken perpendicular to the axis of the radiation beam. Numerous systems exist for producing such a circumferential collimation, some of which use multiple sliding shutters which, piecewise, may generate a radio-opaque mask of arbitrary outline.

As part of collimating the beam to the outline of the tumors, the offset angle of the radiation beam, with respect to a radius line between the radiation source and the center of rotation of the radiation source, may be adjusted to allow the treated area to be other than at the center of rotation. Simultaneously changing the offset angle and the width of the radiation beam as a function of gantry angle allows tumorous tissue having an irregular cross-section within a plane parallel to the radiation beam to be accurately targeted. The width and offset angle of the radiation beam may be controlled by the use of a multiple-leaf collimator.

Adjustment of the offset angle, center, and size of the radiation beam at various gantry angles allows considerable latitude in controlling the dose. Nevertheless, these approaches still impart a considerable amount of undesired dose to healthy tissue, especially where the tumor is concave or highly irregular.

SUMMARY OF THE INVENTION

The present invention is a compensator that dynamically controls the effective intensity of rays within the radiation beam to produce a fluence profile of arbitrary shape. This ability to vary the intensity of individual rays within the beam, as opposed to simply turning them on or off, allows an advanced technique of therapy planning to be employed in which the fluence profiles are varied at each gantry angle to accurately control the dose to irregularly shaped tumors within the body. An efficient iterative approach allows precise calculation of the needed fluence profiles.

Specifically, the compensator includes a number of radiation attenuating leaves in a rack positioned within the radiation beam before it enters the patient. The leaves fit within a plurality of adjacent sleeves in the rack for moving into the radiation beam in a closed state (each leaf thus occluding one ray of the beam) and moving out of the radiation beam in an open state to allow unobstructed passage of the associated ray.

A motivation mechanism allows the leaves to be independently moved between the open and closed state and a timer communicating with the motivation mechanism controls the ratio of the period of time during which each leaf is in the closed state to the period during which each leaf is in the open state to control the average intensity of each ray of the beam.

It is one object of the invention to provide a simple and reliable means for producing an arbitrary fluence profile within a high energy radiation beam. Moving the leaves of the compensator rapidly in and out of the beam allows effectively continuous control of the intensity of the rays.

It is another object of the invention to provide a method of attenuating the individual rays of a high energy radiation beam with negligible effect on the spectrum of the radiation, such as would occur if varying thicknesses of filter material were used. The leaves may be constructed to provide nearly complete blockage of the radiation and thus to prevent "beam hardening" effects where higher energy radiation is preferentially propagated (as is the case with attenuating filters). The ability to use a motivating mechanism that may simply move the leaves between two states, eliminates the need for complex and spatially precise actuating and verification mechanisms.

It is another object of the invention to provide a compensator that provides highly resolved control of the intensity of radiation received throughout a volume of a patient. The compensator may operate on a fan beam of radiation and the patient may be translated with respect to that fan beam to allow control of radiation intensity throughout an irradiated volume. The use of a fan beam allows the motivating mechanism for the compensator leaves to be near the leaves without interfering with the projected radiation.

Fluence profiles, such as may be controlled by the above compensator, may be calculated by a therapy planning apparatus receiving a desired dose map of radiation doses within a volume of the patient. A deconvolver produces a "terma" map from this dose map, of primary total energy released (terma) in the patient. The terma map is calculated so that when the terma values are convolved with scatter, the dose of the desired dose map would be produced. The terma map is used to derive a fluence map from which the fluence profile may be determined.

It is another object of the invention to provide a method of controlling the compensator by producing fluence profiles that accurately account for the interaction and scattering of high energy radiation as it passes through the body. The kernel used for the deconvolution produces terma values that reflect scatter as it influences the desired dose.

It is yet another object of the invention to provide an apparatus for performing radiation therapy planning that takes advantage of the data available from computed tomography systems and the like to accurately account for variations in the density of the patient in computing the optimal dose. The conversion of the terma map to a fluence map may accept values indicating the attenuation caused by each volume element of the patient, from a CT scanner or the like, to accurately derive fluence.

The deconvolver may receive a spatially invariant, isotropic, compact kernel indicating the combined scatter from a number of beams at different gantry angles. The deconvolution may be performed by taking the inverse Fourier transform of the ratio of the Fourier transform of the desired dose map divided by the Fourier transform of the kernel. Alternatively, the deconvolution to a terma map may be performed as part of a projection used to produce the fluence profile, by a fast inversion filter.

It is thus a further object of the invention to provide a rapid means of calculating the terma distribution from the desired dose map employing the computational efficiencies of the fast Fourier transform or of projection mathematics.

The therapy planning apparatus may also include a backprojector receiving the fluence profile and estimating the actual dose map produced. This actual dose map is then received by a residual dose calculator which compares the desired dose map to the actual dose map to produce a residual dose map. An iterator then recalculates the fluence profile based on an error fluence profile produced from the residual dose map.

It is thus a further object of the invention to compensate for errors in the fluence profile introduced by the elimination of negative fluence values such as may be produced in the deconvolution. The iteration, and filtration in projection space, reduces these errors to an acceptable amount.

The foregoing and other objects and advantages of the invention will appear from the following description. In the description, reference is made to the accompanying drawings which form a part hereof and in which there is shown by way of illustration several preferred embodiments of the invention. Such embodiments do not necessarily represent the full scope of the invention, however, and reference must be made therefore to the claims herein for interpreting the scope of the invention.

DETAILED DESCRIPTION OF THE PREFERRED EMBODIMENT

Figure 1:
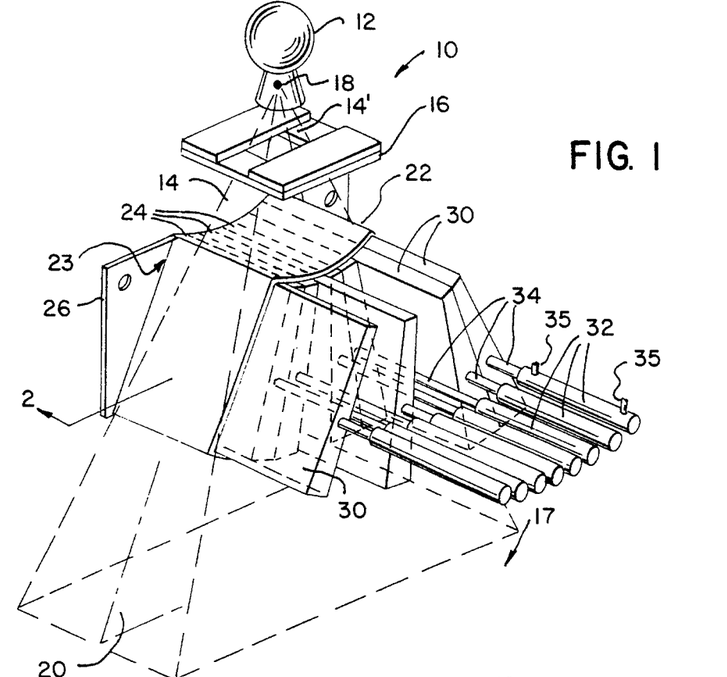
FIG. 1 is a perspective view of the compensator assembly used in the present invention, showing the compensator leaves and their associate pneumatic cylinders.

Referring to FIG. 1, a radiation therapy unit 10 suitable for use with the present invention includes a radiation source 12 producing a generally conical radiation beam 14' emanating from a focal spot 18 and directed towards a patient 17 (not shown in FIG. 1). The conical beam 14' is collimated by a radiation opaque mask 16 constructed of a set of rectangular collimator blades to form a generally planar fan beam 14 centered about a fan beam plane 20.

I. The Compensator

A compensator 22 is centered in the fan beam 14 and about the fan beam plane 20, prior to the radiation being received by the patient 17, and includes a plurality of adjacent trapezoidal leaves 30 which together form an arc of constant radius about the focal spot 18. The leaves 30 are held in sleeves 24. The sleeves 24 are constructed of radio translucent materials and attached at their inner ends 23 to a mounting plate 26 which is fixed relative to the focal spot 18. The mounting plate 26 is constructed of a sturdy, radiopaque material and is positioned just outside the fan beam 14 to prevent interference with the fan beam 14.

Figure 2:
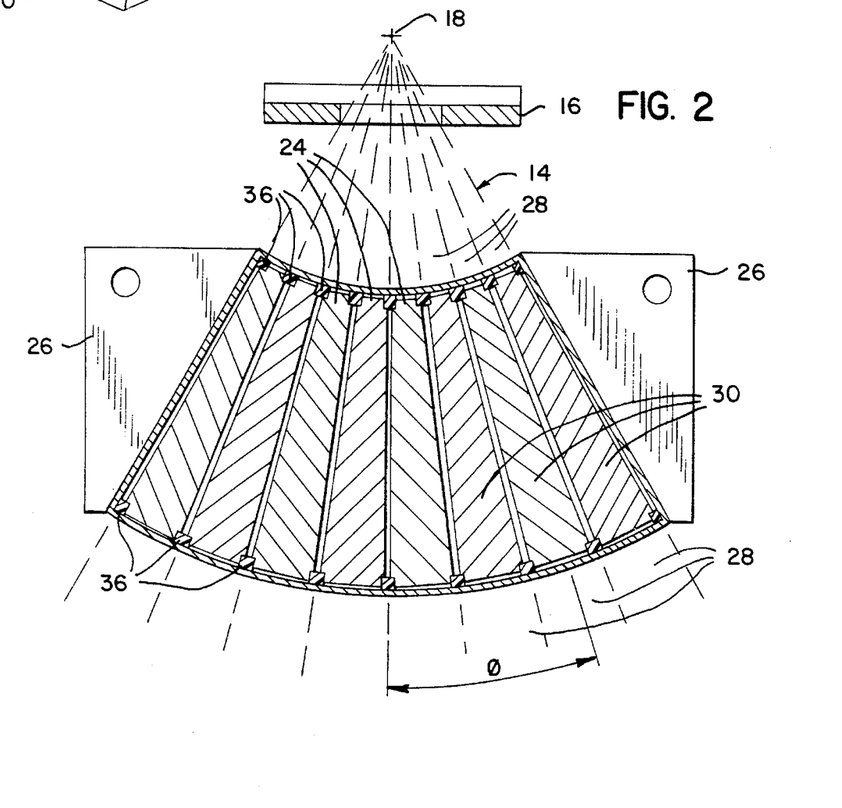
FIG. 2 is a cross-section of the compensator assembly of FIG. 1 along line 2—2 showing the trapezoidal aspect of each compensator leaf, for a fan beam of radiation, and the guide rails for supporting the compensator leaves when they move.

Preferably, the leaves 30 of the compensator 22 subtend the entire fan beam 14 to divide the fan beam 14 into a set of adjacent slab-like rays 28 at offset angles $\phi$. Referring also to FIG. 2, each sleeve 24 is open at its outer end to receive, by sliding, a comparably sized trapezoidal leaf 30 constructed of a dense, radiopaque material such as lead, tungsten, cerium, tantalum or a related alloys.

Each leaf 30 may slide completely within its corresponding sleeve 24 to block the ray 28 associated with that sleeve 24. When the leaf 30 blocks its corresponding ray 28, it is referred to as being in a "closed state". The sleeves 24 are of ample length to permit each leaf 30 to slide out of the path of the fan beam 14, so as to leave its corresponding ray 28 completely unobstructed, and yet to still be guided by the sleeve 24. In this non-blocking position, a leaf is referred to as being in the "open state".

Each leaf 30 may be moved rapidly between its open and closed states by means of a corresponding pneumatic cylinder connected to the leaf 30 by a flexible link 34. The pneumatic cylinders 32 have internal pistons (not shown) that may be moved at high velocity between the ends of the cylinders 32 by means of pressurized air coupled to the cylinders 32 through supply hoses 35. The supply hoses 35 are fed by a compensator control (not shown in FIGS. 1 or 2) to be described below. The pneumatic cylinders 32 are capable of applying high forces to the leaves 30 to move them rapidly and independently between the open and closed states.

Figure 3:
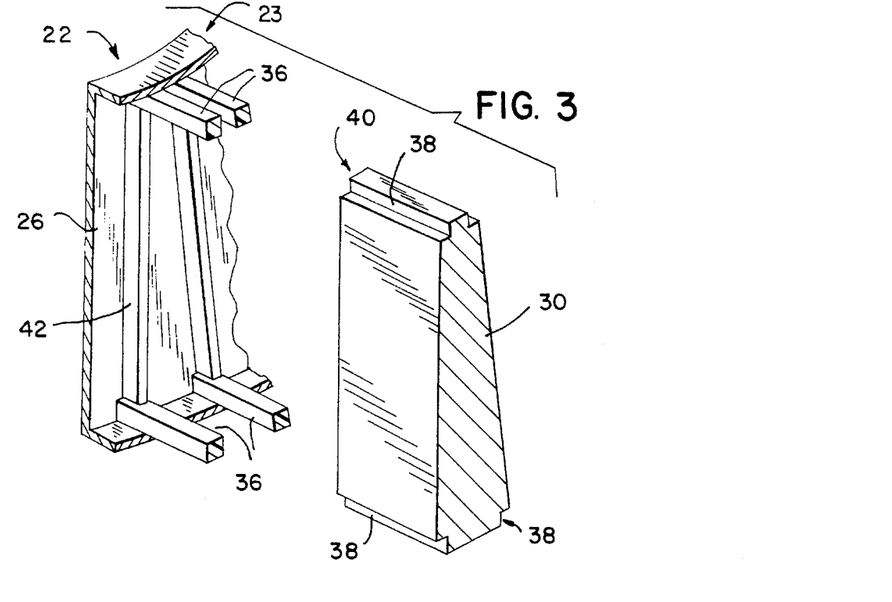
FIG. 3 is a cutaway perspective view of a set of guide rails and one leaf of FIG. 2 showing a collar for supporting the leaf in its fully closed position.

Referring now to FIGS. 2 and 3, the leaves 30 are supported and guided within the sleeves 24 by guide rails 36 fitted into notches 38 cut along the edges of the leaves 30. The notches 38 allow the guide rails 36 to slidably retain the leaves 30 within the sleeves 24 during motion between the open and closed states.

In the closed state, the inner end 40 of each leaf 30 is captured by a rigid collar 42 attached to the mounting plate, which aligns the leaf 30, more accurately than may be done by the guide rails 36, with the mounting plate 26 and hence with the fan beam 14. Whereas the guide rails 36, which are ideally radio translucent, are relatively insubstantial, in contrast, the collar 42, positioned outside the fan beam 14 on the mounting plate 26, need not be radio-translucent and hence is more substantial in construction. A collar (not shown) similar to collar 42, supports each leaf 30 when it is fully in the open state. Because the leaves 30 spend most of their time fully in the open or closed states, they are, at most times, firmly located by a supporting collar 42.

II. Radiation Therapy Hardware

Figure 4:
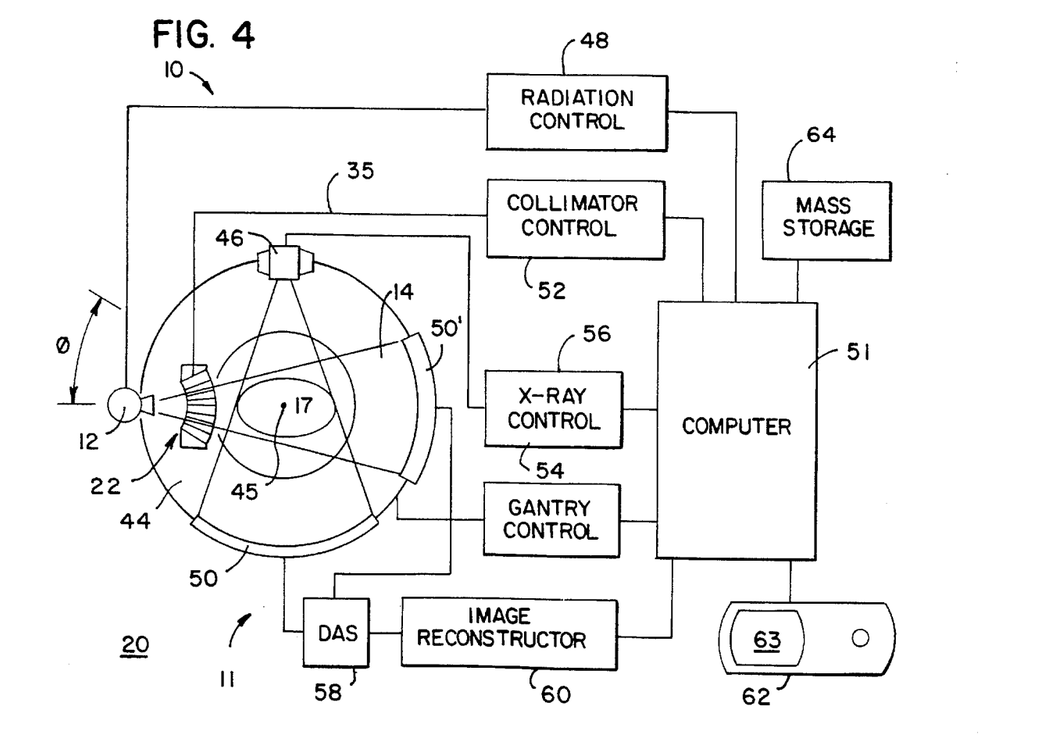
FIG. 4 is a block diagram showing the elements of a radiation therapy apparatus incorporating a conventional CT scanner and the compensator of the present invention and including a computer suitable for controlling that compensator per the present invention.

Referring now to FIG. 4, the radiation source 12 is mounted on a gantry 44, the latter rotating within the fan beam plane 20 about a center of rotation 45 in the patient 17 so that the fan beam 14 may irradiate a slice of the patient 17 from a variety of gantry angles θ.

The radiation source 12 is controlled by a radiation control module 48 which turns the radiation beam 14 on or off under the control of a computer 51.

A compensator control module 52 provides a source of compressed air and valves to gate that air through supply hoses 35 to control, separately, the pneumatic cylinders 32 to move each of the leaves 30 in and out of its corresponding sleeve 24 and ray 28 (see also FIG. 1). The compensator control module 52 also connects with computer 51 to allow program control of the compensator 22 to be described.

A tomographic imaging system 11 employing an x-ray source 46 and an opposed detector array 50 may be advantageously mounted on the same gantry 44 as the radiation source 12 to produce a tomographic or slice image of the irradiated slice of the patient 17 prior to radiation therapy for planning purposes. Alternatively, such tomographic imaging may be performed on a separate machine and the slices aligned according to fiducial points on the patient 17.

A gantry control module 54 provides the signals necessary to rotate the gantry 441and hence to change the position of the radiation source 12 and the angle θ of the fan beam 14 for the radiation therapy, as well as for the computed tomography x-ray source 46 and detector array 50 also attached to gantry 44. Gantry control module 54 connects with computer 51 so that the gantry may be rotated under computer control and also to provide the computer 51 with a signal indicating the gantry angle θ to assist in that control.

Control modules for the tomographic imaging system 11 includes x-ray control module 56 for turning on and off the x-ray source 46, and data acquisition system 58 for receiving data from the detector array 50 in order to construct a tomographic image. It will be understood to one of ordinary skill in the art that a detector array 50' may also be placed to receive radiation from the radiation sourced 12 through the patient 17 to assist in verification of the treatment.

An image reconstructor 60 typically comprising a high speed array processor or the like receives the data from the data acquisition system 58 in order to assist in "reconstructing" a tomographic image from such data according to methods well known in the art. The image reconstructor 60 also communicates with computer 51 to assist in high speed computations used in the present invention as will be described below. The tomographic image allows verification of the patient setup just prior to radiation therapy treatment.

A terminal 62 comprising a keyboard and display unit 63 allows an operator to input to programs and data to the computer 51 and to control the radiation therapy and tomographic imaging equipment 10 and 11 and to display tomographic images produced by the image reconstructor 60 on the display 63. A mass storage system 64, being either a magnetic disk unit or tape drive, allows the storage of data collected by the tomographic imaging system 11 for later use.

Computer programs for operating the radiation therapy system 10 will generally be stored in mass storage unit 64 and leaded into the internal memory of the computer 51 for rapid processing during use of the system 10.

During operation of the radiation therapy unit 10, the compensator control module 52 receives from the computer 51 a fluence profile for each gantry angle. The fluence profile describes the intensity or fluence of each ray 28 of the radiation beam 14 from the radiation source 12 that is desired for that gantry angle θ at a given position of the patient support table (not shown) as translated through the radiation beam 14. Together, the fluence profiles for each gantry angle make up a treatment sinogram for a particular position of the patient table.

The compensator control module 52 moves the leaves 30 of the compensator 22 rapidly between their open and closed states to either fully attenuate or provides no attenuation to each ray 28. Gradations in the fluence of each ray, as needed for each fluence profile, are obtained by adjusting the relative duration during which each leaf 30 is in the closed position compared to the relative duration during which each leaf 30 is in the open position, for each gantry angle. The ratio between the closed and open states or the "duty cycle" for each leaf 30 affects the total energy passed by a given leaf 30 at each gantry angle and thus controls the average fluence of each ray 28. The ability to control the average fluence at each gantry angle permits accurate control of the dose provided by the radiation beam 14 through the irradiated volume of the patient 17 by therapy planning methods to be described below.

The fluence profiles of the treatment sinogram are determined by therapy planning software (described below) and stored in the computer 51.

III. Therapy Planning Software

The generation of a treatment sinogram needed to obtain the full benefits of the above described compensator is performed by specially developed software running on the computer 51 and reconstructor 60. Although the treatment planning is performed in software, it will be recognized that the planning may also be implemented in discrete electronic circuitry dedicated to this operation and that such dedicated circuitry may be employed to provide even greater speed to this process.

Referring to FIG. 5(*a*), the generation of the desired treatment sinogram to control compensator 22 begins with the definition of a desired dose map 66. A typical desired dose map 66 assigns a relatively high radiation dose, within a dose constraint, to an area of tumorous tissue and a second lower radiation dose to the area of healthy tissue outside of that region. The healthy tissue may include an area including a radiation sensitive organ or the like to which an even lower radiation dose may be assigned.

Figure 5A:
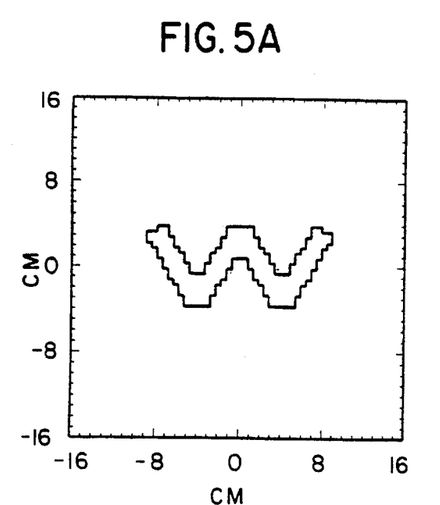
FIGS. 5(a)–(d) are dose distributions of a hypothetical tumorous region showing dose intensity by lines of equal dose, with FIG. 5(a) showing a desired dose distribution and FIGS. 5(b), (c), and (d) showing progressive actual dose distributions after two, three and ten iterations per present invention.
Figure 5B:
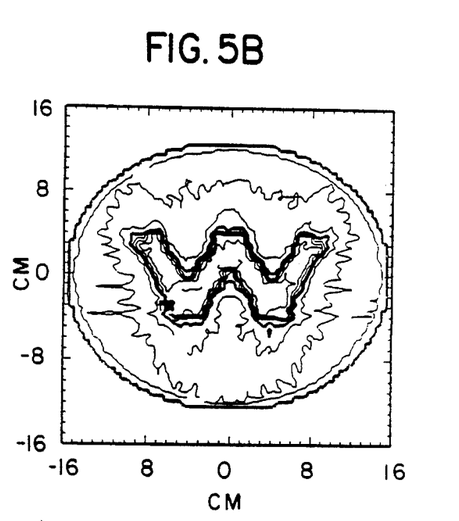
Figure 5C:
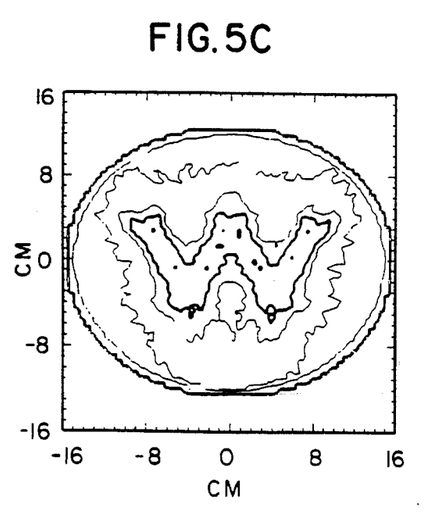
Figure 5D:
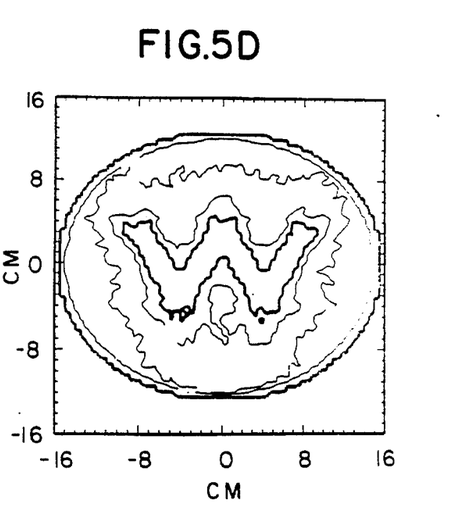

The desired dose map 66 is stored within the memory of computer 51 as an array of elements each element holding one digital value, and may be most easily entered by displaying the tomographic view of the slice of patient 17 on the display 63 of the terminal 62 and manually tracing around the tumorous area using of a track-ball or similar input device, as is well understood in the art. Standard area-filling computer programs may be used to transfer the dose values assigned to each traced region to the appropriate element in the array of memory representing the desired dose map 66.

Figure 6:
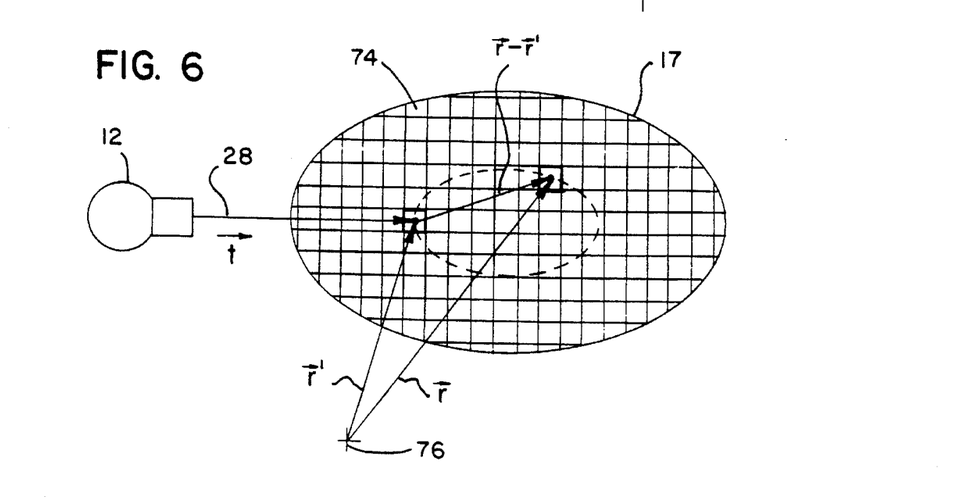
FIG. 6 is a diagrammatic representation of a patient receiving radiation therapy, showing the scatter kernel and the coordinate system used to describe the present invention.

Each element of the dose map 66 thus defines the dose desired at each of the plurality of volume elements 74 ("voxels") within a slice of the patient 17. Referring to FIG. 6, each voxel 74 of the patient 17 may be identified by a vector $\vec{r}$ defined from a given reference point 76. The dose at each voxel 74 is $D(\vec{r})$.

A. Converting Dose to Terma

1. Terma

Generally, the dose at any voxel $\vec{r}$ will depend on the energy received at that voxel $\vec{r}$ from radiation scattered from adjacent voxels $\vec{r}'$ (where adjacent voxels $\vec{r}'$ include the voxel $\vec{r}$, i.e., the radiation received directly from the radiation source 12). The dose $D(\vec{r})$ for a given voxel $\vec{r}$ is given by the following formulas $$D(\vec{r}) = \int T(\vec{r}')A(\vec{r}-\vec{r}')d^3\vec{r}' \quad (1)$$

where $T(\vec{r}')$ is a value indicating the magnitude of the primary total energy released from $\vec{r}'$ per unit mass of that voxel $\vec{r}'$ and is called the "terma" (total energy released per unit mass).

For a monoenergetic external radiation source, the terma rate $\dot{T}(\vec{r})$ is described by, $$T(r') = \frac{\mu}{\rho}(r')E\int\phi(r')dt \quad (2)$$

where $\frac{\mu}{\rho}$ is an effective mass attenuation value at the voxel $\vec{r}'$, E is the energy of the radiation photons in Joules, $\phi$ is the distribution of the fluence rate (flux density). The integration of energy times fluence rate over time is energy fluence $$\psi(\vec{r}')$$

where, $$\psi(\vec{r}') = E\int\phi(\vec{r}')dt \quad (3)$$

hence $$T(\vec{r}') = \frac{\mu}{\rho}(\vec{r}')\psi(\vec{r}') \quad (4)$$

Equation (4) basically relates how much energy from the ray 28 interacts with the voxel $\vec{r}'$.

2. Convolution Kernel $A(\vec{r}-\vec{r}')$ is a convolution kernel describing non-stochastic energy transport or scattering in a uniform medium. $A(\vec{r}-\vec{r}')$ thus describes how the energy from each voxel $\vec{r}'$ spreads to contribute to the dose at voxel $\vec{r}$.

The kernel $A(\vec{r}-\vec{r}')$ may be generated using a Monte Carlo method as is generally understood in the art. As mentioned, it is a three-dimensional function indicating the fraction of energy absorbed at voxel $\vec{r}$ per unit of energy released at voxel $\vec{r}'$. The energy emitted from the terma of each voxel $\vec{r}'$ finds it source in a directed ray 28 from external radiation source 12 and thus $A(\vec{r}-\vec{r}')$ is generally anisotropic as suggested in FIG. 7, spreading outward away from the entry of ray 28. Energy conservation requires that:

$$\int A(\vec{r}')d^3\vec{r}' = 1.0 \quad (5)$$

That is, if the energy transferred by the primary interaction were all deposited on the interaction point, the kernel would be approximated as a delta function.

Figure 7:
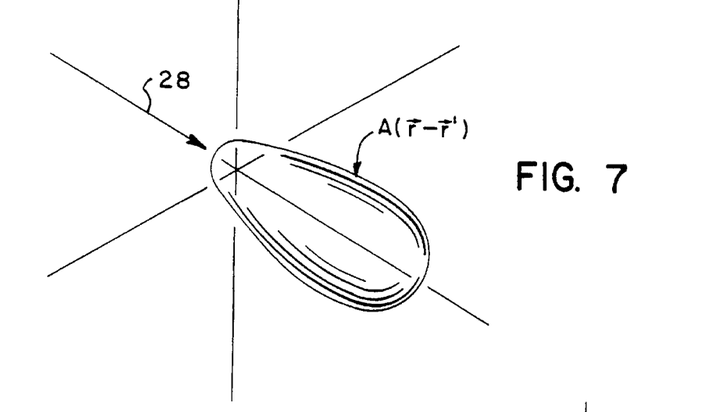
FIG. 7 is a perspective representation of a monodirectional scatter kernel associated with a radiation beam at one gantry angle.

Referring still to FIG. 7, the anisotropy of $A(\vec{r}-\vec{r}')$ is related to the gantry angle $\theta$ and thus of the angle of incidence of the ray 28 at $\vec{r}'$. If the gantry angles $\theta$ at which the patient 17 is irradiated are predetermined, a multidirection convolution kernel $B(\vec{r}-\vec{r}')$, shown in FIG. 8, may be created from weighted superimposition of the kernels $A(\vec{r}-\vec{r}')$.

Figure 8:
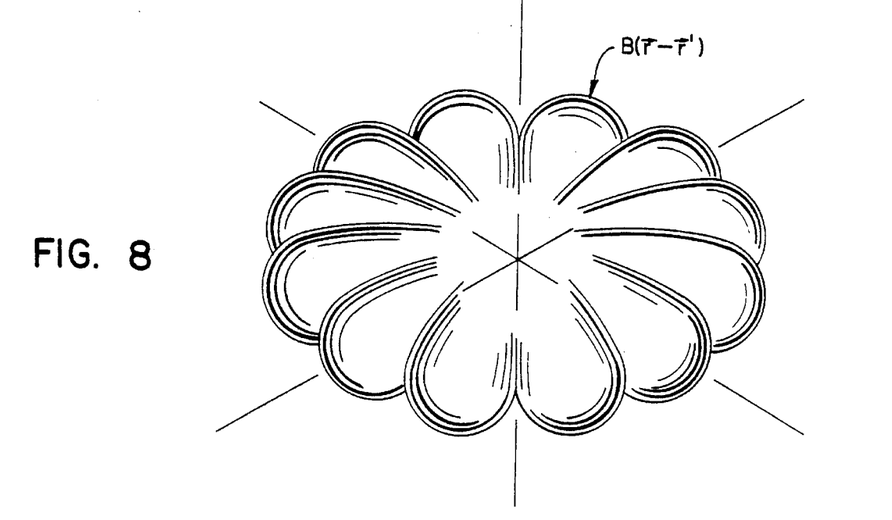
FIG. 8 is a perspective representation of a composite multidirectional scatter kernel associated with a plurality of radiation beams at multiple gantry angles.

Referring to FIG. 8, assuming that the spreading of radiation is approximately equal for all beam directions and the rays 28 from each gantry angle $\theta$ contribute equally to the terma at voxel $\vec{r}\,'$, then the multidirectional convolution kernel reduces to a "isotropic" form as follows:

$$B(\vec{r}-\vec{r}\,') = \frac{1}{n} \sum_{i=1}^{n} A(\vec{r}-\vec{r}\,')_i \qquad (6)$$

where n is the number of discrete gantry angles from which rays 28 are projected.

For multiple rays 28 at different gantry angles, the total dose at a given voxel $\vec{r}$ is the sum of doses from each constituent beam is therefore:

$$D(\vec{r}) = \int T(\vec{r}\,') B(\vec{r}-\vec{r}\,') d^3\vec{r}\,' \qquad (7)$$

where $T(\vec{r}\,') = nT(\vec{r}\,')_i$, the latter term being the contributed portion of the terma for the ith gantry angle.

This simplification assumes that the contribution to the terma from each ray 28 is equivalent and takes advantage of the distributive property of convolution. Errors in this assumption are reduced by the filtration to be discussed later.

Equation (7) substantially simplifies the calculation of dose from terma but still requires a convolution for each voxel $\vec{r}$ times the total number of voxels $\vec{r}\,'$ to calculate the dose over the entire patient volume. Preferably, therefore, the calculational efficiency of the fast Fourier transform can be used and equation (7) converted to the following:

$$D(\vec{r}) = F^{-1}\{F\{T(\vec{r}\,')\} \cdot F\{B(\vec{r}-\vec{r}\,')\}\} \qquad (8)$$

where F and $F^{-1}$ symbolize Fourier and inverse Fourier transforms respectively. This simplification of equation (8) requires that the kernel $B(\vec{r}-\vec{r}\,')$ be spatially invariant and relies on the convolution theorem which states that convolution of two spatially invariant quantities in a space domain is equivalent to multiplication in the frequency domain.

The assumption of the spatial invariance of $B(\vec{r}-\vec{r}\,')$ is correct only to a first order approximation. Typically, the kernel $B(\vec{r}-\vec{r}\,')$ for an external radiation source 12 is a complex function of: (1) beam hardening of a polyenergetic x-ray beam (i.e., the effect of the filtration of the patient 17 in increasing the proportion of high frequency or high energy radiation components), (2) the number of rays 28 crossing each voxel, and (3) exponential attenuation by the patient mass.

In the preferred embodiment, this first factor, beam hardening, is neglected because it is an effect smaller than the attenuation problem. Thus, the photon energy spectrum in the patient 17 may be assumed to be the same as that of the external radiation source 12. This simplification is not required, however, and it will be understood that beam hardening could be accurately accounted for by representing a photon energy spectrum by a finite number of separately convolved energy intervals.

The second factor, the difference in the number and orientation of rays 28 that cross each voxel, caused by the geometry of a finite number of gantry angles and the fan orientation of the beam 14, affect spatial invariance. Problems arising from the fan orientation of the beam (in contrast to a parallel beam geometry) are largely solved if there is a full rotation of the gantry 44. Errors resulting from the fact that irradiation is performed at only a finite number of gantry angles have been determined to be acceptable.

The third factor affecting the assumption of spatial invariance is the attenuation of the medium. This affects the fractional contribution of the total terma from the beams at each gantry angle. Accordingly, in those steps of the planning procedure, as will be noted below, where accurate calculation of dose is critical, the dose distribution is calculated separately for each beam based on the attenuation of overlying voxels, such attenuation deduced from the parameters of the tomographic image. In this case the simplification of equation (8) may not be employed and repeated convolutions must be performed. In certain steps in the planning process, however, as will be noted, an estimate is sufficient and in these cases $B(\vec{r}-\vec{r}\,')$ is assumed to be spatially invariant and the dose calculated according to equation (8).

Production of terma values from a desired dose map 66 is then simply the process of inverting equation (8) as follows:

$$T(\vec{r}) = F^{-1}\left\{\frac{F\{D(\vec{r})\}}{F\{B(\vec{r}-\vec{r}\,')\}}\right\} \qquad (9)$$

This inversion requires that there be no significant "zeros" (typically at high frequencies) in the denominator term $F\{B(\vec{r}-\vec{r}\,')\}$ or more simply that the kernel $B(\vec{r}-\vec{r}\,')$ be spatially compact (i.e., the Fourier transform of a spatially compact kernel will have significant high frequency content). It has been determined by the present inventors that the kernels dictated for patients 17 are sufficiently compact to allow this Fourier deconvolution.

Figure 9:
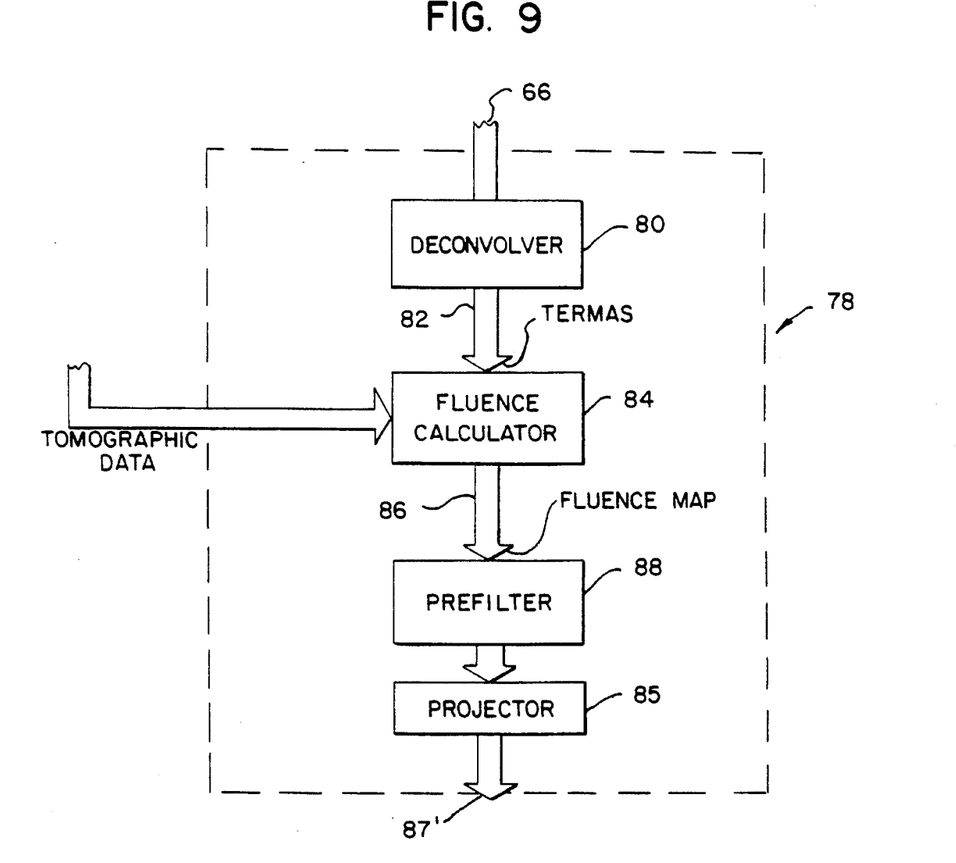
FIG. 9 is a block diagram depicting the fluence profile calculator which takes a desired dose map and calculates a fluence profile.
Figure 10:
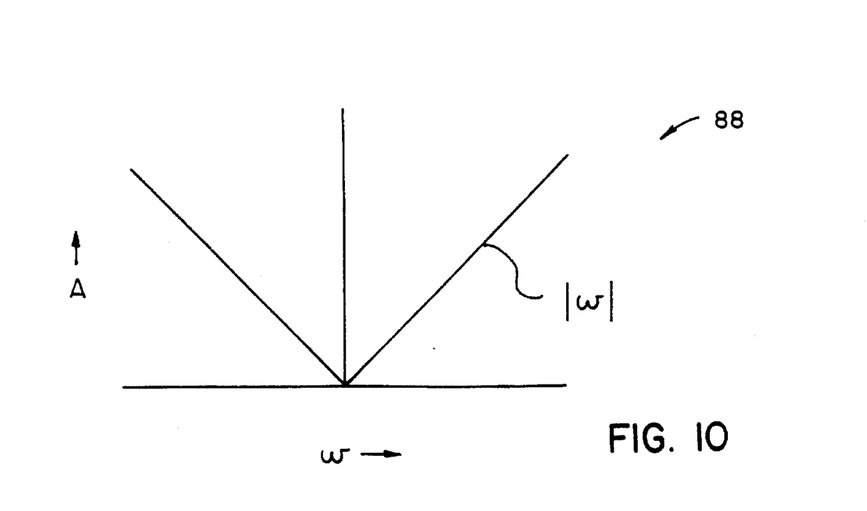
FIG. 10 is a graph showing the prefilter characteristics associated with the fluence profile calculator of FIG. 9.

Referring now to FIG. 9, this deconvolution to produce a terma map 82, giving the terma for each voxel $\vec{r}\,'$, from the desired dose map 66, is represented by process block 80.

B. Converting Terma to Voxel Energy Fluence

Knowing the terma map 82, the energy fluence $\psi(\vec{r}\,')$, which is a measure of the beam intensity, can be determined at each corresponding voxel by equation (4) from a knowledge of $\mu/\rho$ as follows:

$$\Psi(\vec{r}) = \frac{\frac{\mu}{\rho}(\vec{r})}{T(\vec{r})} \qquad (10)$$

The value of $\mu/\rho$ may be estimated and considered a constant or actual $\mu/\rho$ may be deduced from the tomographic scan data collected by means of the tomographic imaging system 11, (shown in FIG. 4). In this manner and as illustrated by process block 84 of FIG. 9, a fluence map 86 giving the fluence at each point of the terma map may be determined.

C. Converting Voxel Energy Fluence to Energy Fluence Profile

The energy fluence $\psi(\vec{r}\,')$ at each voxel $\vec{r}\,'$ is related to the energy of the ray 28 exiting the compensator 22 by the relation:

$$\Psi(\vec{r}) = \Psi_0(\phi,\theta) e^{-\int \mu/\rho(\vec{r}) \rho(\vec{r}) \delta(p-\hat{r}\cdot\vec{r}) dt} \left(\frac{SSD^2(\phi,\theta)}{|\vec{r}|^2}\right) \qquad (11)$$

where $\psi_0(\phi,\theta)$ is the energy fluence for a given ray 28 as described by $\delta(p-\hat{r}\cdot\vec{r})$ at the exit of the compensator 22 and serves to define the fluence profile of the compensator and $\theta$ and $\phi$ are the gantry angle and the offset angles of the ray 28 as previously described.

The exponential term represents the attenuation of the ray 28 from the exit of the compensator 22 to the voxel $\vec{r}$ caused by the mass of the patient 17 where by $\mu/\rho(\vec{r})$ is the attenuation for each voxel $\vec{r}$ along the ray 28, $\rho(\vec{r})$ is the density of each voxel $\vec{r}$, $SSD(\phi,\theta)$ is the distance between the exit of the compensator 22 and the surface of the patient 17, $\hat{r}$ is a unit vector along $\vec{r}$ (where the origin of $\vec{r}$ is now assumed to be the center of rotation of the gantry 45), and p is the perpendicular distance from the gantry's center of rotation 45 and the ray 28. The vector $\vec{t}$ is simply a vector along the ray 28 to provide an integration variable.

The fluence at each voxel $\vec{r}$ is related to the fluence of the radiation beam 14 emitted from the compensator 22 by equation (11). In the preferred embodiment, the density and attenuation of each voxel $\vec{r}$, $\mu/\rho(\vec{r})$ and $\rho(\vec{r})$ are assumed to be constant and the fan beam of radiation is approximated by a parallel beam, hence $$\frac{SSD^2(\phi,\theta)}{|\vec{r}|^2} = 1$$

Borrowing from the mathematics of tomographic image reconstruction, the fluence map 86 may be "reverse" back projected (i.e. projected) by projector 85 to determine a fluence profile to be produced by the external-source necessary to generate the desired fluence map and hence dose.

This projection is simply the opposite of a typical back projection used to form an image of a tomographic slice of a patient 17 from a series of projections taken in a tomographic imaging system. Because a projection is a line integral across a distribution, the energy fluence distribution for each voxel (equation (11)) is first differentiated with respect to the rayline $\vec{t}$:

$$\frac{d\Psi(\vec{r})}{dt} = \left[ \frac{\mu}{\rho}(\vec{r})\rho(\vec{r})\delta(p - \hat{r}\cdot\vec{r}) + \frac{2}{t} \right] \Psi(\vec{r}) \qquad (12)$$

The line integral of $$\frac{d\Psi(\vec{r})}{dt}$$

along $\vec{t}$, corrected for attenuation and inverse-square fall off, then represents the projection operation and $\psi_0(\phi,\theta)$, the fluence profile over the offset angles $\phi$ of each gantry angle $\theta$, is:

$$\Psi_0(\phi,\theta) = \int \left[ \frac{\mu}{\rho}(\vec{r})\rho(\vec{r})\delta(p - \hat{r}\cdot\vec{r}) + \frac{2}{t} \right] \times \qquad (13)$$

$$(\Psi(\vec{r}) e^{+\int\mu/\rho(\vec{r})\rho(\vec{r})\delta(p-\hat{r}\cdot\vec{r})d\vec{t}}\left(\frac{|\vec{r}|^2}{SSD^2(\phi,\theta)0}\right) \times \delta(p - \hat{r}\cdot\vec{r})d\vec{t}$$

The projection of equation (13) is represented by projector 85 in FIG. 9.

The projection process, for the purpose of computing fluence profiles for the compensator 22, differs in a fundamental way from the simple inverse of tomographic back projection. The difference is primarily in a concern for the sharpness in the transition of the dose between the irradiated tumorous tissue 68 and the healthy tissue 70. Sharpness in this transition region reduces the irradiation of healthy tissue 70 and is preferred over actual fidelity of the dose to the desired dose map 66.

For this reason, the fluence map 86 from the fluence calculator 84 is prefiltered as shown by process block 88 to produce a filtered fluence map $\psi'(\phi,\theta)$ as follows:

$$\psi'(\phi,\theta) = F-1\{F\{\psi(\phi,\theta)|\omega|\}+ \qquad (14)$$

where $\psi(\phi,\theta)$ is the fluence map 86 and $|\omega|$ is a ramp filter in frequency space and the '+' subscript indicates the positive component of the filtering result. This prefilter 88 serves to increase the high frequency content of the fluence map 86 and thus to aid in rapid transition of dose at the tumor/non-tumor interface.

It is noted that this prefilter 88 is similar to the filter used in tomographic imaging's "filtered" back projection. That is, like tomographic imaging, the filter de-emphasizes the low frequency components of the projection in producing image data. In addition other prefilters may be applied to correct for the use of the radially symmetric kernel (equation (6)) in computing the dose map from the terma map composed from the fluence profile In practice the computation of a terma map, the generation of a fluence map and the calculation of the fluence profiles need not be performed as discrete steps but may be accomplished by a direct projection of the dose map with appropriate filtering. The filtering is accomplished by a "fast inversion filter" which combines in projection space the operation of deconvolution and ramp filtration.

This may be symbolically specified by the following equation $$\psi(\phi,\theta) = \rho\{D(\vec{r})\} \otimes I(t) \qquad (15)$$

where $\rho$ refers to a projection operation and $I(t)$ is the fast inversion filter. The $\otimes$ operators refers to a convolution operation such as would normally be done in Fourier space using a fast Fourier transformation.

Referring still to FIG. 9, the fluence profile calculations of block 78, including the deconvolver 80, the fluence calculator 84, the prefilter 88 which includes any projection space filter (such as a ramp filter, a fast inversion filter followed by truncation of zeros), and the projector 85 thus produce fluence profiles which together create an estimated treatment sinogram 87' from the desired dose map 66. The fluence profile calculator 78 may use the Fourier convolution of equation (9) in the estimate of the fluence profiles at this stage, accepting minor inaccuracies in that process, to be corrected at a later stage, as will be described below.

D. Iteration

Figure 11:
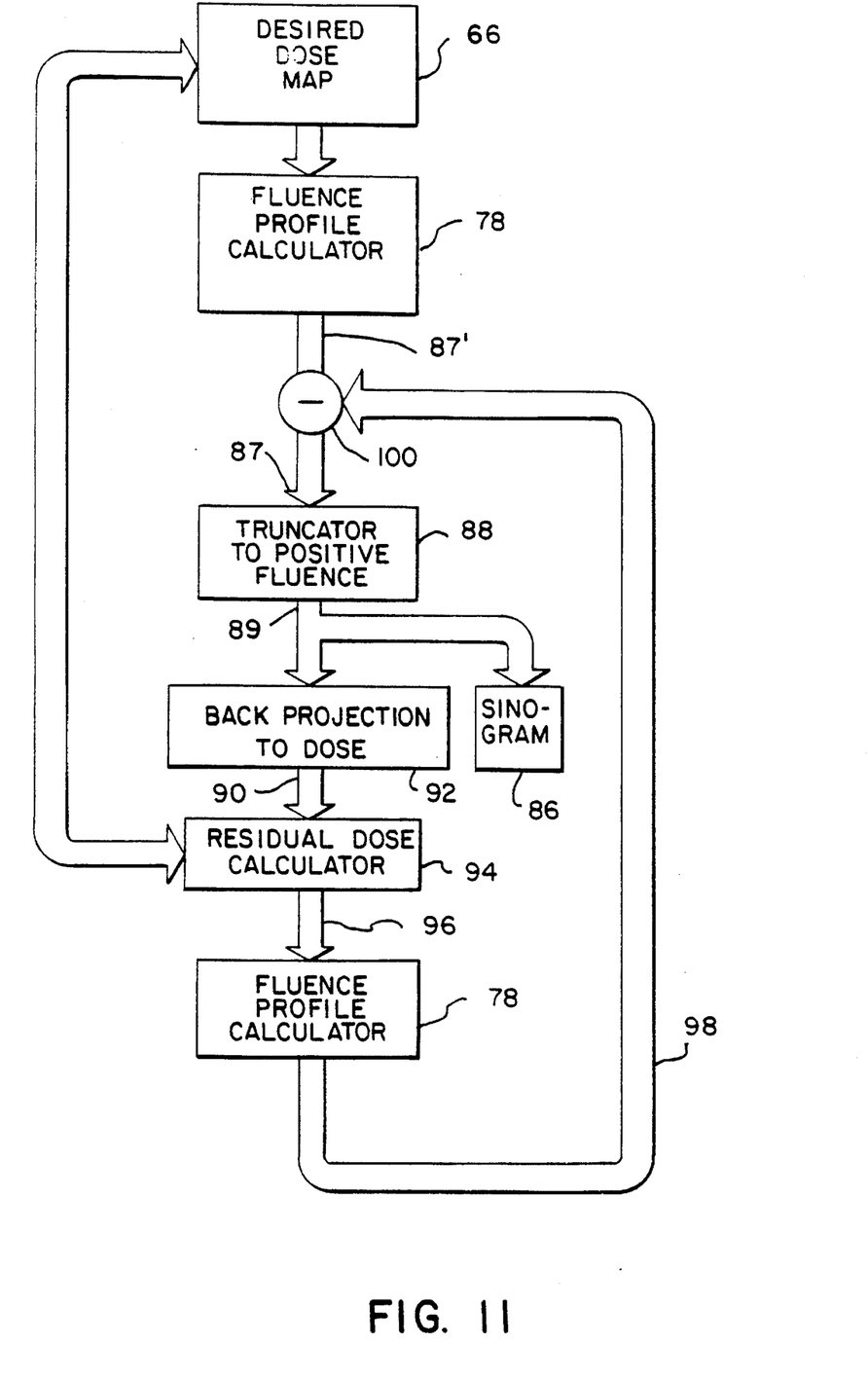
FIG. 11 is a block diagram depicting the overall iterative method of controlling the compensator of the present invention, employing the fluence profile calculation method of FIG. 9.

Referring now to FIG. 11, the fluence profile calculator 78 converts the desired dose map 66 to an estimated treatment sinogram 87', however the fluence profiles of this estimated treatment sinogram 87' may not be used to control the compensator 22 because, in general, the estimated treatment sinogram 87 will include positive and negative values of fluence. Only positive values of fluence are physically realizable by the compensator 22; a negative value of fluence would represent a ray 28 that absorbed radiation along its path which is physically unrealizable.

Accordingly, at process block 88, the fluence values of the estimated treatment sinogram 87' are truncated to positive fluence values 89. As a result of this truncation, the estimated treatment sinogram 87' no longer produces the desired dose map.

The amount of error resulting from the truncation producing the positive fluence profiles 89 is determined by back projecting the positive fluence values 89 to an actual dose map 90 deviating from the desired dose map 66. This back projection is accomplished by computing a fluence map from the positive fluence values 89 per equation (11) and a terma map per equation (4) and then convolving the terma map with the kernel per equation (7) to establish the actual dose map 90 per process block 92 of FIG. 11.

In this back projection, the assumption of spatial invariance of the convolution kernel $B(\vec{r}-\vec{r}')$ is not made so as to produce a more accurate actual dose map 90.

The projection of a fluence profile onto a patient 17 to compute a dose map may be performed by a number of other procedures known to those of ordinary skill in the art.

The actual dose map 90 is compared to the desired dose map 66 to produce residual dose map 96 as indicated by process block 94. In the preferred embodiment, the comparison subtracts from the values of each voxel $\vec{r}$ of the actual dose map 90, the greater of: a) the corresponding value of desired dose map 66, or b) a predetermined upper dose constraint. The predetermined upper dose constraint is a threshold number that is deemed an acceptable dose to tumorous tissue 68. Clearly, other methods of quantifying the difference between the desired dose map and the actual dose map will be apparent from this description to those of ordinary skill in the art.

Figure 12A:
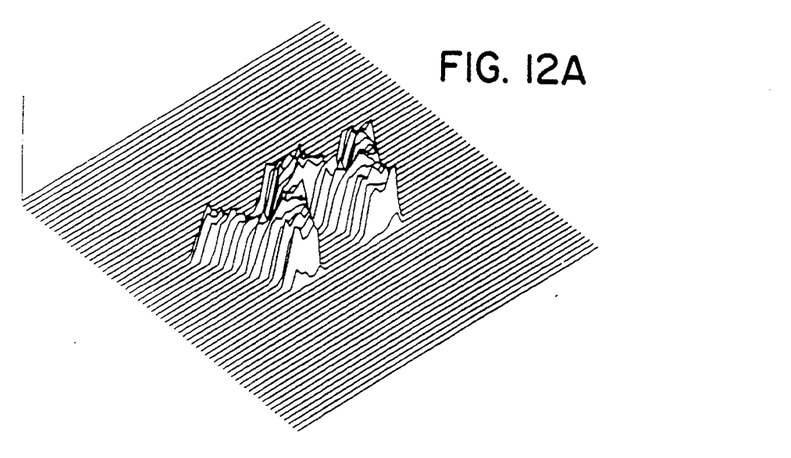
FIGS. 12(a)–(c) are perspective views of plots showing the error between the desired dose distribution and the actual dose distribution obtained with the present invention for one, two and four steps of iteration respectively.

The result of this comparison process 94 is to produce a residual dose map 96 shown in FIG. 12(*a*). This residual dose map 96 is then, again, operated on by the fluence profile calculator 78 (in lieu of the desired dose map 66) to produce an error fluence profile 98 (in lieu of the estimated treatment sinogram 87).

A thus produced error fluence profile 98 is subtracted by subtracter 100 from the estimated treatment sinogram 87' to produce a new estimated treatment sinogram 87.

Figure 12B:
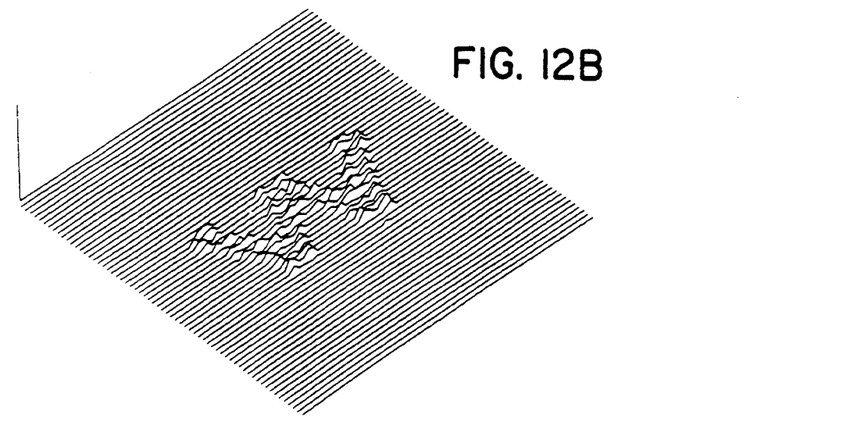
Figure 12C:
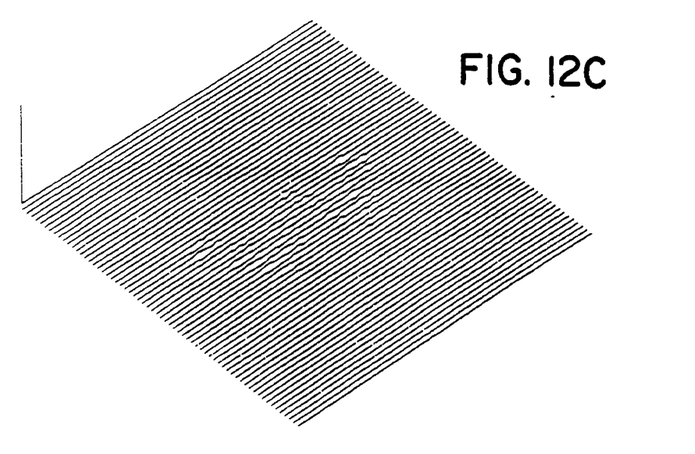

As shown in FIG. 11, this new estimated treatment sinogram 87 is repeatedly operated on by process block 88, 92, 94 and 78 for a predetermined number of iterations, the magnitude of the error fluence profile 98 values decreasing with each iteration as shown in FIGS. 12(*b*)–(*d*) until a suitably low error fluence profile 98 is obtained.

The the new estimated fluence profile 87 is then truncated per process block 88 to produce a final sinogram 91 for use in controlling the compensator 22 as previously described.

Referring again to FIGS. 5(*b*), (*c*) and (*d*), dose maps obtained by the present invention corresponding to a desired dose map 66 of FIG. 5(*a*) are shown after: one iteration (FIG. 5(*b*)); two iterations (FIG. 5(*c*)); and ten iterations (FIG. 5(*d*)). The variations in dose in the target volume shown in FIG. 5(*d*) are plus or minus 2% about the predetermined upper limit of 1,000 cGy.

The above description has been that of a preferred embodiment of the present invention. It will occur to those who practice the art that many modifications may be made without departing from the spirit and scope of the invention. For example, a computed tomography system need not be incorporated with the radiation therapy equipment but separate such equipment could be used. The relationship between the terma values and the fluence values may assume a constant density of the patient to eliminate the need for a precise tomographic scan of the irradiated area. Clearly the method for planning radiation therapy is not limited to a particular radiation source but may be used with any radiation source which may be decomposed into separately attenuated radiation rays. In order to apprise the public of the various embodiments that may fall within the scope of the invention, the following claims are made:

We claim:

1. A method of radiation therapy planning for an external beam of radiation having a plurality of adjacent rays, the fluence of each ray together defining a fluence profile, comprising the steps of:

(a) obtaining a x-ray computed tomography image of a slice in a slice plane through a body including a tumor to be treated;

(b) defining a dose map with respect to the x-ray computed tomography image indicating desired doses within the slice of the body and the tumor; and (c) determining a treatment sinogram of fluence profiles for a range of angles about the patient within the slice plane based on the dose map and the effect of the varying composition of the body on the absorption of radiation from the external beam of radiation as revealed in the x-ray computed tomography image.

2. In a radiation therapy device having a radiation source for producing a radiation beam directed toward a volume of a patient at a plurality of gantry angles, the beam including a plurality of adjacent rays, the fluence of each ray together defining a fluence profile, a therapy planning apparatus comprising:

an input means for receiving a desired dose map of desired radiation doses within the volume of the patient;

a deconvolution means for producing a terma map, corresponding to the desired dose map, indicating energy release values and locations in the volume that with scatter, would produce the dose of the desired dose map;

a fluence calculator receiving the terma map and for determining the fluence of the rays at the locations to produce a fluence map; and a projection means receiving the fluence values and combining the fluence values to produce the fluence profile corresponding to the desired dose map.

3. The therapy planning apparatus as recited in claim 2 wherein the deconvolution means, fluence calculator and projection means are implemented by convolving a fast inversion filter with a projection of the desired dose map, the fast inversion filter incorporating the convolution kernel for deducing the terma map.

4. The therapy planning apparatus as recited in claim 2 including a prefilter for filtering the fluence map prior to the projection by the projection means.

5. The therapy planning apparatus as recited in claim 2 including a second input means for receiving an attenuation map of the volume and wherein the fluence calculator produces a fluence map based on the attenuation map.

6. The therapy planning apparatus as recited in claim 2 wherein the deconvolution means produces the terma map by calculating the inverse Fourier transform of the ratio of the Fourier transform of the desired dose map divided by the Fourier transform of a kernel representing the spreading of the radiation from each location.

7. The therapy planning apparatus as recited in claim 6 where the kernel reflects the spreading caused by radiation beams at a plurality of predetermined gantry angles.

8. The therapy planning apparatus as recited in claim 2 including:

a back-projector receiving the fluence profile and estimating the actual dose map produced;

a residual dose calculator for comparing the desired dose map to the actual dose map to produce a residual dose map; and an iteration means for recalculating the fluence profile based on a error fluence profile produced from the residual dose map.

9. The therapy planning apparatus as recited in claim 8 wherein the residual dose calculator produces the residual dose map by comparing from the actual dose map with the desired dose map.

10. The therapy planning apparatus as recited in claim 8 wherein the iteration means provides residual dose map to the deconvolution means and the fluence calculator to calculate the error fluence profile in the same manner as the fluence profile is calculated from the desired dose map and wherein the fluence profile is recalculated by subtracting the error fluence profile from the fluence profile.

* * * * *

UNITED STATES PATENT AND TRADEMARK OFFICE
CERTIFICATE OF CORRECTION

PATENT NO. : 5,528,650
DATED : June 18, 1996
INVENTOR(S) : Swerdloff et al.

It is certified that error appears in the above-identified patent and that said Letters Patent is hereby corrected as shown below:

Col. 1, line 58      "tumors" should be --tumor--

Col. 6, line 5      "gantry 441" should be --gantry 44--.

Col. 6, line 14      "includes" should be --include:--

Col. 6, line 19      "sourced 12" should be --source 12--

Col. 6, line 42      "leaded" should be —loaded—

Col. 7, line 57      "formulas" should be --formula:--

Col. 8, line 2      "described by," should be --described by:--

Col. 8, line 5

$$\dot{T}(r') = \frac{\mu}{\rho}(r')E \int \dot{\phi}(r')dt$$

should be $$\dot{T}(\vec{r}') = \frac{\mu}{\rho}(\vec{r}')E \int \dot{\phi}(\vec{r}')dt$$

Col. 8, line 18      "where," should be --where:--

Col. 10, line 30      "voxel $\vec{r}'$" should be --voxel $\vec{r}$--

Col. 10, line 64      "$\delta(\rho-\hat{r}_r \cdot \vec{r})$"
should be --$\delta(\rho-\hat{r} \cdot \vec{r})$--

UNITED STATES PATENT AND TRADEMARK OFFICE
CERTIFICATE OF CORRECTION

PATENT NO. : 5,528,650

DATED : June 18, 1996

INVENTOR(S) : Swerdloff et al.

It is certified that error appears in the above-identified patent and that said Letters Patent is hereby corrected as shown below:

Col. 11, line 9      $\hat{r}_r$ is a unit should be --$\hat{r}$ is a unit--

Col. 12, lines 33 and 34      $\Psi(\phi,\theta) = p\{D(\vec{r})\} \otimes I(t)$
should be
--$\Psi(\phi,\theta) = \wp\{D(\vec{r})\} \otimes I(t)$--

Col. 12, line 34      "where p refers"

should be --where $\wp$ refers--

Signed and Sealed this

Nineteenth Day of November, 1996

*Attest:*

BRUCE LEHMAN

*Attesting Officer*      *Commissioner of Patents and Trademarks*